United States Patent
Cheng

(10) Patent No.: US 8,749,897 B2
(45) Date of Patent: Jun. 10, 2014

(54) LARGE-FIELD-OF-VIEW LENS SYSTEM FOR CAPSULE ENDOSCOPE AND CAPSULE ENDOSCOPE HAVING LARGE-FIELD-OF-VIEW LENS SYSTEM

(71) Applicant: OmniVision Technologies, Inc., Santa Clara, CA (US)

(72) Inventor: Ting-Yu Cheng, San Jose, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 52 days.

(21) Appl. No.: 13/671,350

(22) Filed: Nov. 7, 2012

(65) Prior Publication Data
US 2014/0128673 A1    May 8, 2014

(51) Int. Cl.
*G02B 3/02* (2006.01)
*A61B 1/002* (2006.01)

(52) U.S. Cl.
USPC .......................................... 359/716; 600/168

(58) Field of Classification Search
CPC ........... G02B 3/02; A61B 1/002; A61B 1/041
USPC ............................ 359/716; 600/160, 167, 168
See application file for complete search history.

(56) References Cited

U.S. PATENT DOCUMENTS

| | | | |
|---|---|---|---|
| 6,939,295 B2 | 9/2005 | Yokoi et al. | |
| 7,460,315 B1 | 12/2008 | Cheng et al. | |
| 7,518,810 B1 | 4/2009 | Cheng et al. | |
| 7,599,132 B1 | 10/2009 | Cheng et al. | |
| 7,701,650 B2 | 4/2010 | Lin | |
| 7,796,342 B2 | 9/2010 | Baba | |
| 8,125,720 B2 * | 2/2012 | Chang et al. | 359/793 |
| 2011/0286112 A1 * | 11/2011 | Orihara et al. | 359/716 |

* cited by examiner

*Primary Examiner* — Joseph P Martinez
(74) *Attorney, Agent, or Firm* — Lathrop & Gage LLP

(57) ABSTRACT

A lens system and a for a capsule endoscope includes a first lens having a concave aspheric surface having a radius R2 and a second lens having a convex aspheric surface having a radius R3 facing the first lens. A third lens has a convex aspheric surface having radius R6. The lens system satisfies the following conditions: (1) R2/Gap>1 and ABS(R3/R2) >1.28; (2) 1<ABS(R6/R2)<1.1 and R6<0; and (3) V2<V1 and V2<V3; wherein: i) Gap is a distance from a center of curvature of the concave aspheric surface of the first lens to a center of curvature of the convex aspheric surface of the second lens; (ii) ABS denotes absolute value; and (iii) V1 is an Abbe number of the first lens, V2 is an Abbe number of the second lens, and V3 is an Abbe number of the third lens.

23 Claims, 7 Drawing Sheets

LARGE-FIELD-OF-VIEW LENS SYSTEM FOR CAPSULE ENDOSCOPE AND CAPSULE ENDOSCOPE HAVING LARGE-FIELD-OF-VIEW LENS SYSTEM

BACKGROUND

1. Technical Field

This disclosure relates to lens systems for capsule endoscopes having large fields of view and capsule endoscopes having lens systems with large fields of view.

2. Discussion of Related Art

A capsule endoscope is a diagnostic instrument in the form of a swallowable optical imaging device. The instrument is sized to be small enough and shaped such as in the shape of an ellipsoid capsule to be swallowed by the patient. The capsule endoscope is typically provided with one or more light emitting units for providing illumination of a scene being imaged, a wide-angle imaging lens system, an image sensor for receiving raw image data, a processing unit for processing the raw image data, a wireless transceiver for transmitting image data and a power unit such as a battery.

A technician activates the endoscope for imaging, and then the patient being examined swallows the endoscope. As the endoscope passes through the esophagus, stomach and intestines, it gathers and transmits image data. Because of the relatively short time available to gather image data, and the possibility of inconvenient or non-optimal capsule positioning, it is very important that the endoscope be outfitted with high-quality, wide-angle, large-field-of-view optics to increase the possibility of obtaining desirable images.

SUMMARY

According to one aspect, a lens system is provided. The lens system includes a first lens having a concave aspheric surface having a radius R2 and a second lens having a convex aspheric surface having a radius R3 facing the first lens. A third lens has a convex aspheric surface having radius R6. The lens system satisfies the following conditions:

$R2/Gap > 1$ and $ABS(R3/R2) > 1.28$;

$1 < ABS(R6/R2) < 1.1$ and $R6 < 0$;

$V2 < V1$ and $V2 < V3$;

wherein: i) Gap is a distance from a center of curvature of the concave aspheric surface of the first lens to a center of curvature of the convex aspheric surface of the second lens; (ii) ABS denotes absolute value; and (iii) V1 is an Abbe number of the first lens, V2 is an Abbe number of the second lens, and V3 is an Abbe number of the third lens.

According to another aspect, a lens system is provided. The lens system includes a first substrate and a first lens having a planar surface in contact with the first substrate and a concave aspheric surface having a radius R2. The lens system also includes a second substrate and a second lens having a convex aspheric surface having a radius R3 facing the first lens and a planar surface in contact with the second substrate. A third lens has a planar surface in contact with the second substrate and a convex aspheric surface having radius R6. The second substrate is sandwiched between the second lens and the third lens. The lens system satisfies the following conditions:

$R2/Gap > 1$ and $ABS(R3/R2) > 1.28$;

$1 < ABS(R6/R2) < 1.1$ and $R6 < 0$;

$V2 < V1$ and $V2 < V3$;

wherein: i) Gap is a distance from a center of curvature of the concave aspheric surface of the first lens to a center of curvature of the convex aspheric surface of the second lens; (ii) ABS denotes absolute value; and (iii) V1 is an Abbe number of the first lens, V2 is an Abbe number of the second lens, and V3 is an Abbe number of the third lens.

According to another aspect, a capsule endoscope is provided. The capsule endoscope includes a housing, a power source and a lens system. The lens system includes a first lens having a concave aspheric surface having a radius R2 and a second lens having a convex aspheric surface having a radius R3 facing the first lens. A third lens has a convex aspheric surface having radius R6. The lens system satisfies the following conditions:

$R2/Gap > 1$ and $ABS(R3/R2) > 1.28$;

$1 < ABS(R6/R2) < 1.1$ and $R6 < 0$;

$V2 < V1$ and $V2 < V3$;

wherein: i) Gap is a distance from a center of curvature of the concave aspheric surface of the first lens to a center of curvature of the convex aspheric surface of the second lens; (ii) ABS denotes absolute value; and (iii) V1 is an Abbe number of the first lens, V2 is an Abbe number of the second lens, and V3 is an Abbe number of the third lens.

BRIEF DESCRIPTION OF THE DRAWINGS

The foregoing and other features and advantages of the disclosure will be apparent from the more particular description of preferred embodiments, as illustrated in the accompanying drawings, in which like reference characters refer to the same parts throughout the different views. The drawings are not necessarily to scale, emphasis instead being placed upon illustrating the principles of the disclosure.

DETAILED DESCRIPTION

Figure 1:
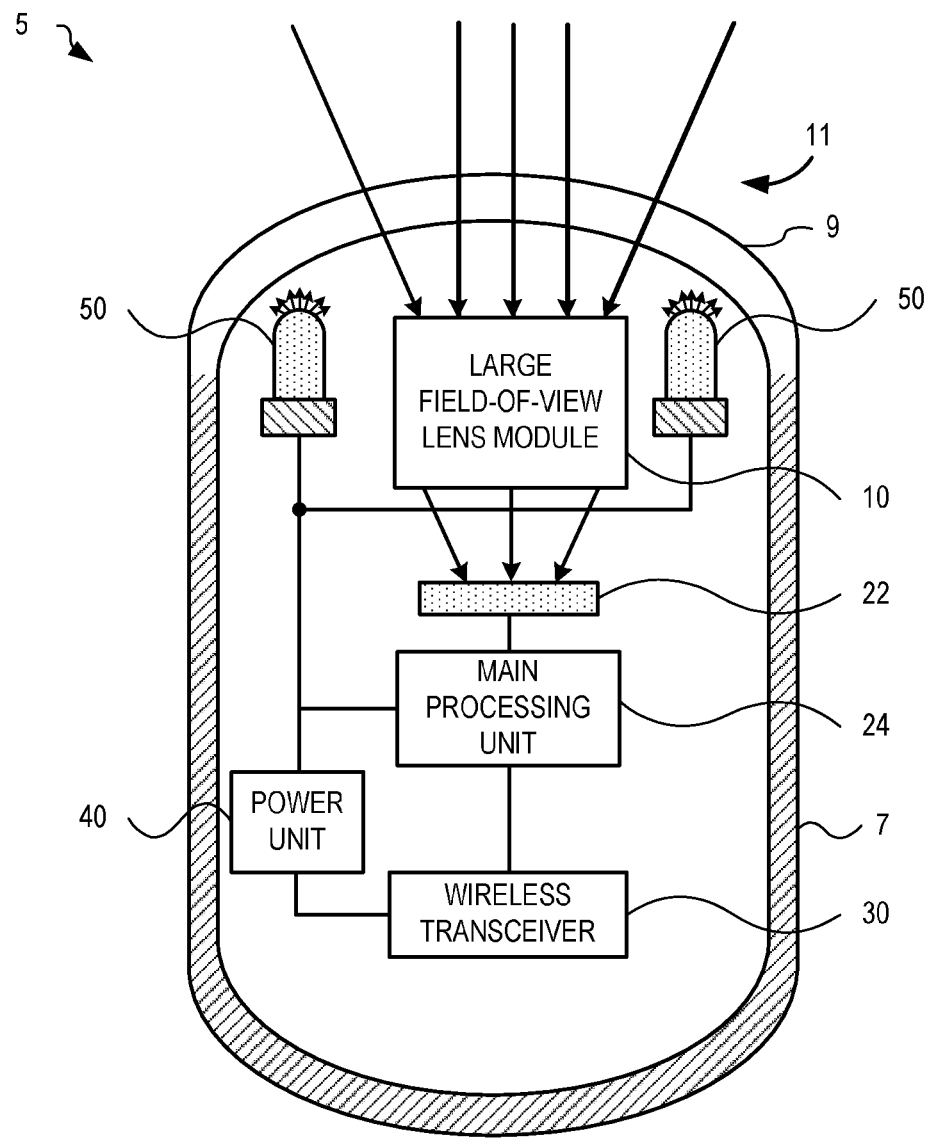
FIG. 1 includes a schematic block diagram of a capsule endoscope, according to some exemplary embodiments.

FIG. 1 includes a schematic block diagram of a capsule endoscope, according to some exemplary embodiments. Referring to FIG. 1, capsule endoscope 5 includes a sealed body 7 in which are contained a large-field-of-view lens module 10, according to some exemplary embodiments described in detail herein. Light 11 returning from an object or scene being imaged, which can be illuminated by lamps 50, passes through a transparent portion 9 of sealed body 7 and impinges on lens module 10. Lens module 10 forms an image on image sensor 22, which converts the received light into electrical signals and transmits them to a main processing unit 24. Main processing unit 24 processes the electrical signals to obtain digital image signals, which may be encoded and transmitted by a wireless transceiver 30, or may be read by other means. All of these subsystems are powered as necessary by a power unit 40, which can include one or more suitable batteries and/or power conditioning/amplifying circuits, as required.

It should be noted that the capsule endoscope configuration illustrated in FIG. 1 is intended to be exemplary only. The present disclosure is applicable to any configuration of capsule endoscope.

As noted above, because of the unique environment in which capsule endoscopes are typically used, including the relatively short time available to gather image data, and the possibility of inconvenient or non-optimal capsule positioning, it is very important that the endoscope be outfitted with high-quality, wide-angle, large-field-of-view optics to increase the possibility of obtaining desirable images. In accordance with exemplary embodiments, it is desirable that the optics of the capsule endoscope comply with at least the following specific exemplary requirements: (1) large field of view (FOV), e.g., larger than 110°, (2) compact size, e.g., on the order of 1.2 mm×1.2 mm×2.1 mm, including the image plane, (3) low cost, e.g., including no more than three lens elements in the lens system, and (4) good optical quality, e.g., having nominal aberrations.

Figure 2:
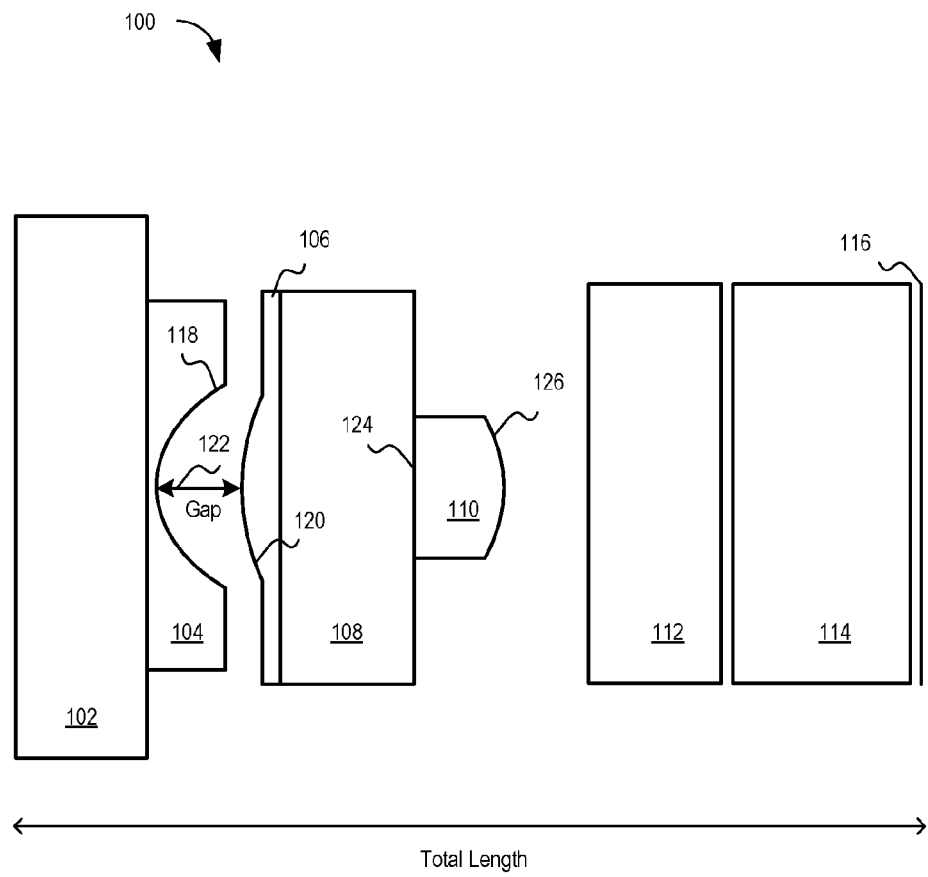
FIG. 2 includes a schematic block diagram of a large-field-of-view lens module, which can be used with a capsule endoscope, according to some exemplary embodiments.

FIG. 2 includes a schematic block diagram of a large-field-of-view lens module, which can be used with a capsule endoscope, according to some exemplary embodiments. Referring to FIG. 2, lens module 100 meets at least the four requirements listed above for the large-field-of-view lens module 10. Lens module 100 includes a first substrate 102, a first lens 104, a second lens 106, a second substrate 108, and a third lens 110. In addition, lens module 100 includes two glass plates 112 and 114 in front of an image plane 116.

First substrate 102 includes two parallel planar surfaces. A first planar surface of first substrate 102 faces toward object space. First lens 104 has a planar surface (radius R1=∞), which is in contact with the second planar surface of first substrate 102. First lens 104 also has a concave aspheric surface 118, which has a radius R2. First substrate 102 and first lens 104 collect incident rays with large incident angles entering lens module 100. Planar-concave first lens 104 mitigates the angle of incident rays that enter module 100, reduces distortion, and reduces the cross-section of the incident rays in module 100.

Second lens 106 has a convex aspheric surface 120 having radius R3 facing first lens 104 and a planar surface (radius R4=∞). Second lens 106 is separated from first lens 104 by a predetermined distance. The predetermined distance between the center of curvature of aspheric surface 118 of first lens 104 and the center of curvature of aspheric surface 120 of second lens 106 defines a "Gap" identified in FIG. 2 by reference numeral 122 between aspheric surface 118 of lens 104 and aspheric surface 120 of second lens 106. In some exemplary embodiments, the medium in gap 122 between first lens 104 and second lens 106 is air. The planar surface of second lens 106 is in contact with second substrate 108, which has two parallel planar surfaces. Second lens 106 conveys the light rays onto a stop 124 of lens module 100.

Third lens 110 has a planar surface (radius R5=∞) in contact with second substrate 108 and a convex aspheric surface 126 having a radius R6. Second substrate 108 is thus sandwiched between second lens 106 and third lens 110. Stop 124 is interposed between second substrate 108 and third lens 110. Third lens 110 leads light rays to arrive at image plane 116 through two glass plates 112 and 114. Glass plates 112 and 114 may be separated by a small distance. Glass plate 114 may be the cover glass of an image sensor. Glass plate 114 and image plane 116 may be separated by a small distance.

Stop 124 located within lens module 100 helps to maintain cones of rays in the field of view symmetric. This in turn helps to maintain the symmetric performance of the modulation transfer function (MTF).

Table 1 shows the lens data of lens module 100 according to the exemplary embodiments illustrated in FIG. 2.

TABLE 1 f = 0.4 mm; F/4; FOV = 118°; Diameter of IMA = 0.938 mm
Nd: Refractive Index; V: Abbe Number

| Lens System | Radius (mm) | Thickness (mm) | Nd | V | Conic | Aspheric Coefficient | | | | |
|---|---|---|---|---|---|---|---|---|---|---|
| | | | | | | 2nd-Order Term | 4th-Order Term | 6th-Order Term | 8th-Order Term | 10th-Order Term |
| OBJ | Infinity | 2.500 | | | | | | | | |
| First Substrate | Infinity | 0.300 | 1.52 | 64 | | | | | | |
| First Lens, R1 | Infinity | 0.021 | 1.51 | 57 | | | | | | |
| First Lens, R2 | 0.25 | 0.200 | | | 0 | 0 | 11.110 | −373.886 | 6863.458 | −82394.455 |
| Second Lens, R3 | 0.55 | 0.089 | 1.59 | 29 | 0 | 0 | 10.878 | −395.008 | 5457.943 | −22112.417 |
| Second Lens, R4 | Infinity | 0.000 | | | | | | | | |
| Second Substrate | Infinity | 0.300 | 1.52 | 63 | | | | | | |
| Stop | Infinity | 0.000 | | | | | | | | |
| Third Lens, R5 | Infinity | 0.210 | 1.51 | 57 | | | | | | |
| Third Lens, R6 | −0.28 | 0.250 | | | 0 | 0 | 23.535 | −2260.475 | 100535.740 | −1457137.7 |
| Glass | Infinity | 0.300 | 1.52 | 64 | | | | | | |
| | Infinity | 0.005 | | | | | | | | |
| Glass | Infinity | 0.400 | 1.52 | 63 | | | | | | |
| | Infinity | 0.010 | | | | | | | | |
| IMA | Infinity | 0.904 | | | | | | | | |

The designed lens data of Table 1 meet the following three conditions.

$R2/\text{Gap}>1$ and $\text{ABS}(R3/R2)>1.28$   Condition (1)

$1<\text{ABS}(R6/R2)<1.1$ and $R6<0$   Condition (2)

$V2<V1$ and $V2<V3$   Condition (3)

V1, V2, and V3 are the Abbe numbers of first lens 104, second lens 106, and third lens 110, respectively. ABS denotes the absolute value. R2, R3, and R6 are the radii of the aspheric surfaces of first lens 104, second lens 106, and third lens 110, respectively. Gap is the distance from the center of curvature of aspheric surface 118 of first lens 104 to the center of curvature of aspheric surface 120 of second lens 106.

Figure 3A:
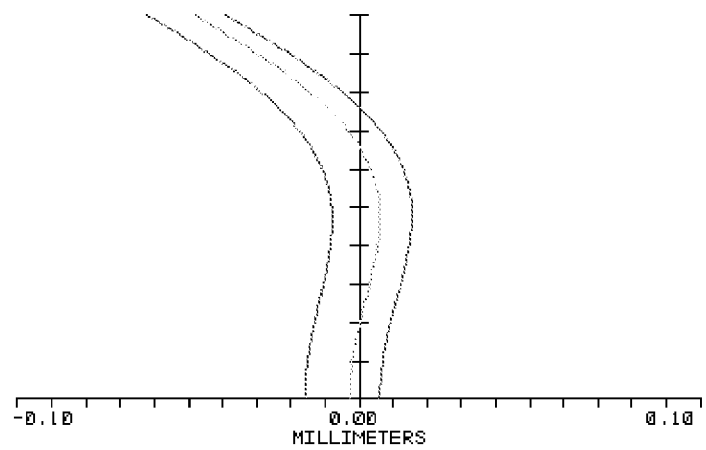
FIGS. 3(a), 3(b), 3(c), and 3(d) are curves which illustrate spherical aberration, field curvature, distortion, and lateral color aberration, respectively, for the lens module illustrated in FIG. 2, according to some exemplary embodiments.
Figure 3B:
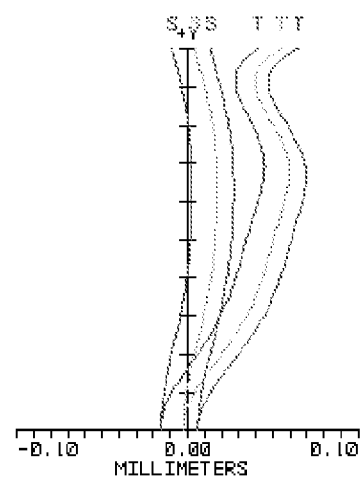
Figure 3C:
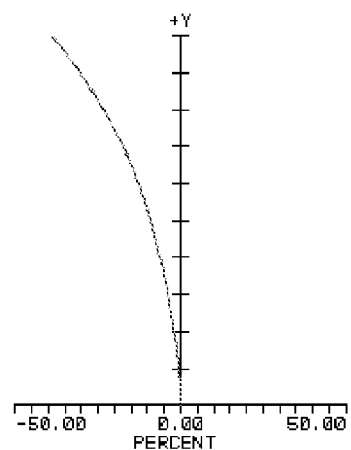
Figure 3D:
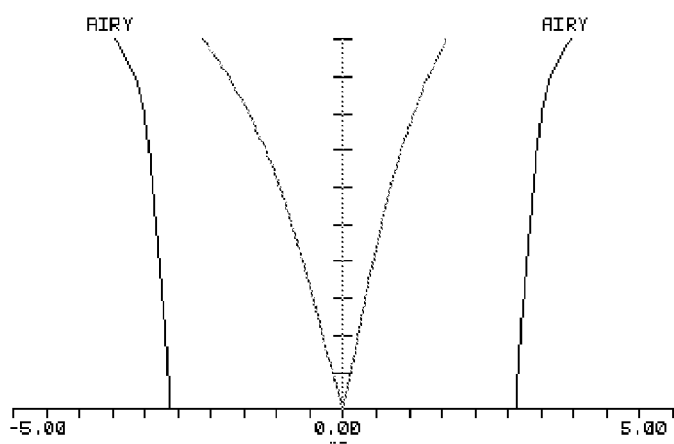

FIGS. 3(a), 3(b), 3(c), and 3(d) are curves which illustrate spherical aberration, field curvature, distortion, and lateral color aberration, respectively, for lens module 100 illustrated in FIG. 2, according to some exemplary embodiments. Referring to FIG. 3(a), the three curves, from left to right, correspond to light with wavelengths of 435.8 nm (f curve), 587.6 nm (d curve), and 656.3 nm (c curve). The spherical aberration is in a possible range which is illustrated to extend from −0.10 mm to 0.10 mm. Referring to the diagram of FIG. 3(b), the field curvature is in a possible range which is illustrated to extend from −0.10 mm to 0.10 mm. Referring to the diagram of FIG. 3(c), the distortion is in a possible range which is illustrated to extend from −50% to 50%. Referring to the diagram of FIG. 3(d), the lateral color aberration is limited within an Airy disk from −5.00 μm to 5.00 μm. The aberration values are nominal as understood by those of ordinary skill in the art.

In some exemplary embodiments, the dimensions of the optics part of lens module 100 that includes first substrate 102, first lens 104, second lens 106, second substrate 108, and third lens 110 are approximately 1.04 mm×1.04 mm×1.12 mm for an overall volume of approximately 1.21 mm³ The total length from the outer surface of the first substrate to the image plane is approximately 2.085 mm, which is less than 2.2 mm. In some exemplary embodiments, lens module 100 uses two substrates and three lens elements. For example, the exemplary embodiments illustrated in FIG. 2 meet the four specific exemplary requirements: (1) large field-of-view (FOV) of about 118°, (2) imaging optics compact size of about 1.04×1.04×2.085 mm (size of the first substrate×total length), (3) low cost since it comprises only three lens elements, and (4) good optical quality of nominal aberration. It is understood that the invention may not be limited by these four exemplary specifications.

In some exemplary embodiments, the focal length of lens module 100 is 0.4 mm, which is less than 0.43 mm, and the F-number is 4. In some exemplary embodiments, the diameter of rays at the image plane is 0.938 mm, which is less than 1 mm. In some exemplary embodiments the conic values of the aspheric surfaces of first lens 104, second lens 106, and third lens 110 are zero.

Figure 4:
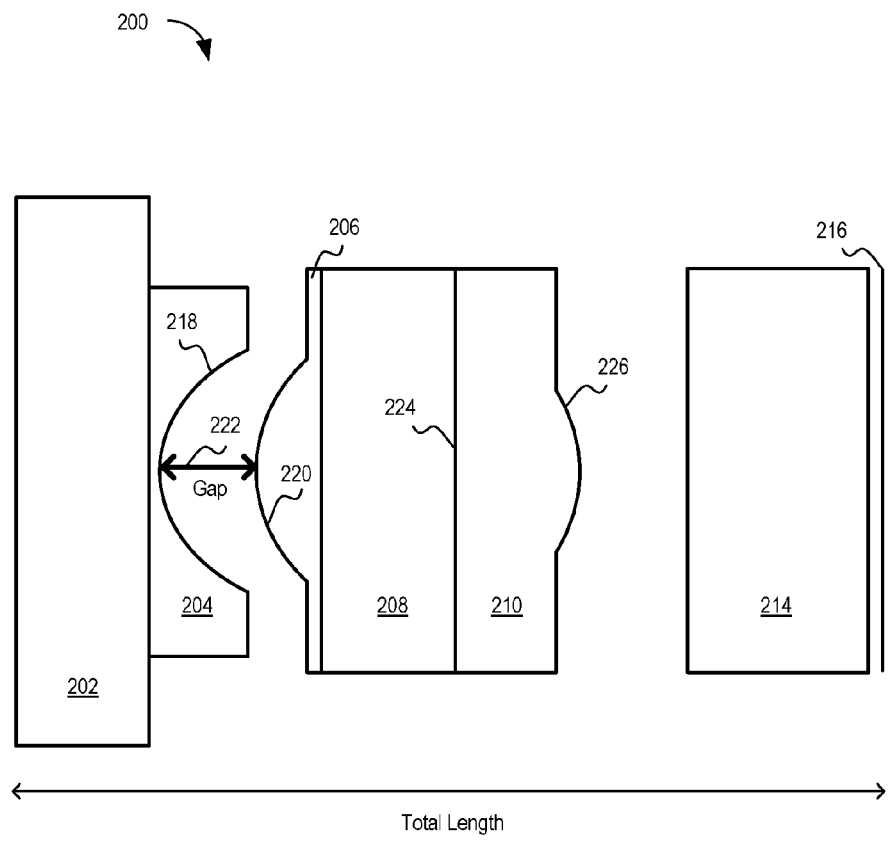
FIG. 4 includes a schematic block diagram of a large-field-of-view lens module, which can be used with a capsule endoscope, according to some other exemplary embodiments.

FIG. 4 includes a schematic block diagram of a large-field-of-view lens module, which can be used with a capsule endoscope, according to some other exemplary embodiments. Referring to FIG. 4, lens module 200 also meets at least the four requirements listed above for the large-field-of-view lens module 10. Lens module 200 includes a first substrate 202, a first lens 204, a second lens 206, a second substrate 208, and a third lens 210. In addition, lens module 200 includes a glass plate 214 in front of an image plane 216.

First substrate 202 includes two parallel planar surfaces. A first planar surface of first substrate 202 faces toward object space. First lens 204 has a planar surface (radius R1=∞), which is in contact with the second planar surface of first substrate 202. First lens 204 also has a concave aspheric surface 218, which has a radius R2.

Second lens 206 has a convex aspheric surface 220 having radius R3 facing first lens 204 and a planar surface (radius R4=∞). Second lens 206 is separated from first lens 204 by a predetermined distance. The predetermined distance between the center of curvature of aspheric surface 218 of first lens 204 and the center of curvature of aspheric surface 220 of second lens 206 defines a "Gap" identified in FIG. 2 by reference numeral 222 between aspheric surface 218 of lens 204 and aspheric surface 220 of second lens 206. In some exemplary embodiments, the medium in gap 222 between first lens 204 and second lens 206 is air. The planar surface of second lens 206 is in contact with second substrate 208, which has two parallel planar surfaces.

Third lens 210 has a planar surface (radius R5=∞) in contact with second substrate 208 and a convex aspheric surface 226 having a radius R6. Second substrate 208 is thus sandwiched between second lens 206 and third lens 210. Stop 224 is interposed between second substrate 208 and third lens 210. Third lens 210 leads light rays to arrive at image plane 216 through glass plate 114. Glass plate 214 may be the cover glass of an image sensor. Glass plate 214 and image plane 216 may be separated by a distance.

Stop 224 located within lens module 200 helps to maintain cones of rays in the field of view symmetric. This in turn helps to maintain the symmetric performance of the modulation transfer function (MTF).

Table 2 shows the lens data of lens module 200 according to the exemplary embodiments illustrated in FIG. 4.

TABLE 2 f = 0.43 mm; F/3.8; FOV = 115°; Diameter of IMA = 0.885 mm
Nd: Refractive Index; V: Abbe Number

| Lens System | Radius (mm) | Thickness (mm) | Nd | V | Conic | Aspheric Coefficient | | | | |
|---|---|---|---|---|---|---|---|---|---|---|
| | | | | | | 2nd-Order Term | 4th-Order Term | 6th-Order Term | 8th-Order Term | 10th-Order Term |
| OBJ | Infinity | 2.500 | | | | | | | | |
| First Substrate | Infinity | 0.300 | 1.52 | 64 | | | | | | |
| First Lens, R1 | Infinity | 0.022 | 1.52 | 49 | | | | | | |
| First Lens, R2 | 0.28 | 0.220 | | | 0 | 0 | 9.555 | −147.014 | 2335.874 | −29378.743 |
| Second | 0.36 | 0.139 | 1.59 | 29 | 0 | 0 | 5.882 | −13.157 | −2307.616 | 27485.646 |

TABLE 2-continued f = 0.43 mm; F/3.8; FOV = 115°; Diameter of IMA = 0.885 mm
Nd: Refractive Index; V: Abbe Number

| Lens System | Radius (mm) | Thickness (mm) | Nd | V | Conic | Aspheric Coefficient ||||| 
| | | | | | | 2nd-Order Term | 4th-Order Term | 6th-Order Term | 8th-Order Term | 10th-Order Term |
|---|---|---|---|---|---|---|---|---|---|---|
| Lens, R3 | | | | | | | | | | |
| Second Lens, R4 | Infinity | 0.000 | | | | | | | | |
| Second Substrate | Infinity | 0.300 | 1.52 | 62 | | | | | | |
| Stop | Infinity | 0.000 | | | | | | | | |
| Third Lens, R5 | Infinity | 0.280 | 1.52 | 49 | | | | | | |
| Third Lens, R6 | −0.34 | 0.242 | | | 0 | 0 | 1.054 | −187.551 | 11155.458 | −153395.63 |
| Glass | Infinity | 0.400 | 1.52 | 62 | | | | | | |
| | Infinity | 0.037 | | | | | | | | |
| IMA | Infinity | 0.886 | | | | | | | | |

The designed lens data of Table 2 also meet the following three conditions set forth above in connection with Table 1.

$$R2/Gap > 1 \text{ and } ABS(R3/R2) > 1.28 \quad \text{Condition (1)}$$

$$1 < ABS(R6/R2) < 1.1 \text{ and } R6 < 0 \quad \text{Condition (2)}$$

$$V2 < V1 \text{ and } V2 < V3 \quad \text{Condition (3)}$$

Figure 5A:
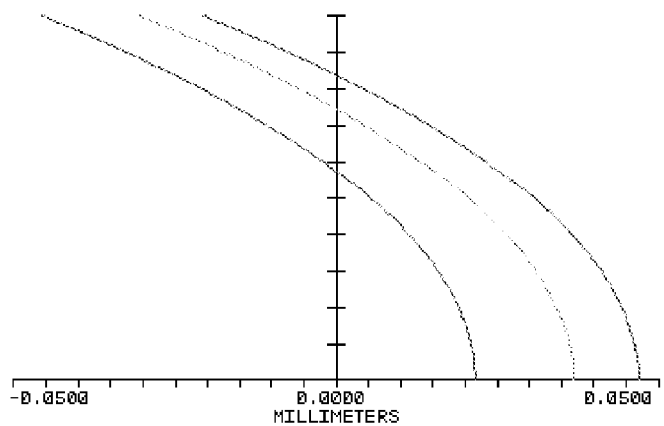
FIGS. 5(a), 5(b), 5(c), and 5(d) are curves which illustrate spherical aberration, field curvature, distortion, and lateral color aberration, respectively, for lens module 200 illustrated in FIG. 4, according to some exemplary embodiments.
Figure 5B:
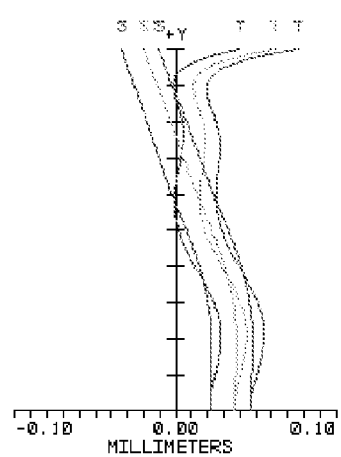
Figure 5C:
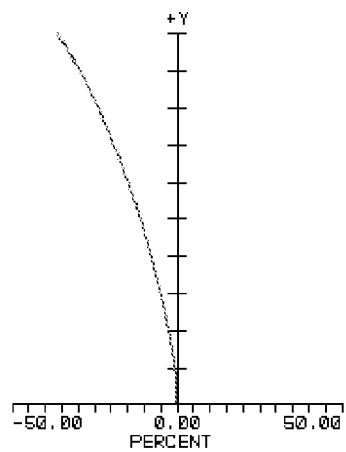
Figure 5D:
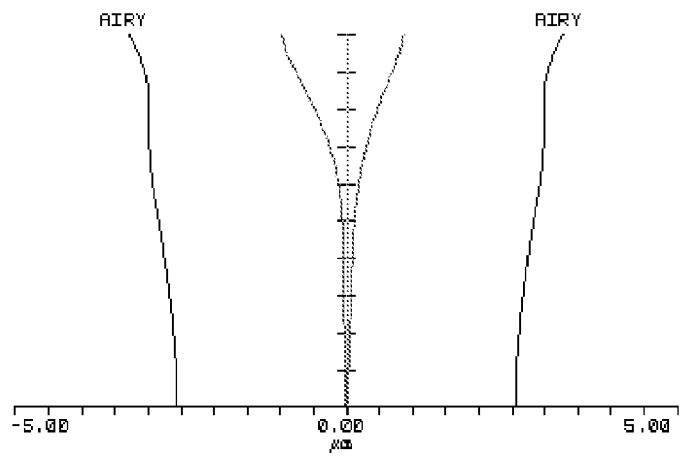

FIGS. 5(a), 5(b), 5(c), and 5(d) are curves which illustrate spherical aberration, field curvature, distortion, and lateral color aberration, respectively, for lens module 200 illustrated in FIG. 4, according to some exemplary embodiments. Referring to FIG. 5(a), the three curves, from left to right, correspond to light with wavelengths of 435.8 nm (f curve), 587.6 nm (d curve), and 656.3 nm (c curve). The spherical aberration is in a possible range which is illustrated to extend from −0.05 mm to 0.05 mm. Referring to the diagram of FIG. 5(b), the field curvature is in a possible range which is illustrated to extend from −0.10 mm to 0.10 mm. Referring to the diagram of FIG. 5(c), the distortion is in a possible range which is illustrated to extend from −50% to 50%. Referring to the diagram of FIG. 5(d), the lateral color aberration is limited within an Airy disk from −5.00 μm to 5.00 μm. The aberration values are nominal as understood by those of ordinary skill in the art.

In some exemplary embodiments, the dimensions of the optics part of lens module 200 that includes first substrate 202, first lens 204, second lens 206, second substrate 208, and third lens 210 are approximately 1.18 mm×1.18 mm×1.261 mm for an overall volume of approximately 1.76 mm$^3$. The total length from the outer surface of the first substrate to the image plane is approximately 1.94 mm. In some exemplary embodiments, lens module 200 uses two substrates and three lens elements. For example, the exemplary embodiments illustrated in FIG. 4 meet the four specific exemplary requirements: (1) large field-of-view (FOV) of about 115°, (2) imaging optics compact size of about 1.18×1.18×1.94 mm (size of the first substrate×total length), (3) low cost since it comprises only three lens elements, and (4) good optical quality of nominal aberration. It is understood that the invention may not be limited by these four exemplary specifications.

In some exemplary embodiments, the focal length of lens module 200 is approximately 0.43 mm, and the F-number is 3.8, which is less than 4. In some exemplary embodiments, the diameter of rays at the image plane is 0.885 mm, which is less than 1 mm. In some exemplary embodiments the conic values of the aspheric surfaces of first lens 204, second lens 206, and third lens 210 are zero.

Combinations of Features

Various features of the present disclosure have been described above in detail. The disclosure covers any and all combinations of any number of the features described herein, unless the description specifically excludes a combination of features. The following examples illustrate some of the combinations of features contemplated and disclosed herein in accordance with this disclosure.

In any of the embodiments described in detail and/or claimed herein, a stop may be interposed between the second substrate and the third lens.

In any of the embodiments described in detail and/or claimed herein, a field of view of the lens system may be greater than 110°.

In any of the embodiments described in detail and/or claimed herein, a total length of the lens system from an outer surface of the first substrate to an image plane may be less than 2.1 mm.

In any of the embodiments described in detail and/or claimed herein, a focal length of the lens system may be equal to or less than 0.43 mm.

In any of the embodiments described in detail and/or claimed herein, an F-number of the lens system may be equal to or less than 4.

In any of the embodiments described in detail and/or claimed herein, a diameter of light rays at an image plane of the lens system may be less than 1.0 mm.

In any of the embodiments described in detail and/or claimed herein, each of the first substrate and the second substrate may have two parallel planar surfaces.

In any of the embodiments described in detail and/or claimed herein, the lens system may be contained within a capsule endoscope.

While the present disclosure has shown and described exemplary embodiments, it will be understood by those of ordinary skill in the art that various changes in form and details may be made therein without departing from the spirit and scope of the present disclosure, as defined by the following claims.

I claim:

1. A lens system, comprising:
   a first lens having a concave aspheric surface having a radius R2;

a second lens having a convex aspheric surface having a radius R3 facing the first lens; and a third lens having a convex aspheric surface having radius R6;

wherein the lens system satisfies the following conditions:

$$R2/Gap>1 \text{ and } ABS(R3/R2)>1.28;$$

$$1<ABS(R6/R2)<1.1 \text{ and } R6<0;$$

$$V2<V1 \text{ and } V2<V3;$$

wherein: i) Gap is a distance from a center of curvature of the concave aspheric surface of the first lens to a center of curvature of the convex aspheric surface of the second lens; (ii) ABS denotes absolute value; and (iii) V1 is an Abbe number of the first lens, V2 is an Abbe number of the second lens, and V3 is an Abbe number of the third lens.

2. The lens system of claim 1, further comprising:
a first substrate; and
a second substrate, the second substrate being sandwiched between the second lens and the third lens.

3. The lens system of claim 2, wherein:
the first lens further comprises a planar surface in contact with the first substrate;
the second lens further comprises a planar surface in contact with the second substrate; and
the third lens further comprises a planar surface in contact with the second substrate.

4. The lens system of claim 3, further comprising a stop interposed between the second substrate and the third lens.

5. The lens system of claim 3, wherein a field of view of the lens system is greater than 110°.

6. The lens system of claim 3, wherein a total length of the lens system from an outer surface of the first substrate to an image plane is less than 2.1 mm.

7. The lens system of claim 3, wherein a focal length of the lens system is equal to or less than 0.43 mm.

8. The lens system of claim 3, wherein an F-number of the lens system is equal to or less than 4.

9. The lens system of claim 3, wherein a diameter of light rays at an image plane of the lens system is less than 1.0 mm.

10. The lens system of claim 3, wherein each of the first substrate and the second substrate has two parallel planar surfaces.

11. The lens system of claim 3, wherein the lens system is contained within a capsule endoscope.

12. A lens system, comprising:
a first substrate;
a first lens having a planar surface in contact with the first substrate and a concave aspheric surface having a radius R2;
a second substrate;
a second lens having a convex aspheric surface having a radius R3 facing the first lens and a planar surface in contact with the second substrate; and
a third lens having a planar surface in contact with the second substrate and a convex aspheric surface having radius R6;
wherein the second substrate is sandwiched between the second lens and the third lens;
wherein the lens system satisfies the following conditions:

$$R2/Gap>1 \text{ and } ABS(R3/R2)>1.28;$$

$$1<ABS(R6/R2)<1.1 \text{ and } R6<0;$$

$$V2<V1 \text{ and } V2<V3;$$

wherein: i) Gap is a distance from a center of curvature of the concave aspheric surface of the first lens to a center of curvature of the convex aspheric surface of the second lens; (ii) ABS denotes absolute value; and (iii) V1 is an Abbe number of the first lens, V2 is an Abbe number of the second lens, and V3 is an Abbe number of the third lens.

13. The lens system of claim 12, wherein the lens system is contained within a capsule endoscope.

14. A capsule endoscope, comprising:
a housing;
a power source;
a lens system, comprising:
    a first lens having a concave aspheric surface having a radius R2;
    a second lens having a convex aspheric surface having a radius R3 facing the first lens; and
    a third lens having a convex aspheric surface having radius R6;
    wherein the lens system satisfies the following conditions:

$$R2/Gap>1 \text{ and } ABS(R3/R2)>1.28;$$

$$1<ABS(R6/R2)<1.1 \text{ and } R6<0;$$

$$V2<V1 \text{ and } V2<V3;$$

wherein: i) Gap is a distance from a center of curvature of the concave aspheric surface of the first lens to a center of curvature of the convex aspheric surface of the second lens; (ii) ABS denotes absolute value; and (iii) V1 is an Abbe number of the first lens, V2 is an Abbe number of the second lens, and V3 is an Abbe number of the third lens.

15. The capsule endoscope of claim 14, wherein the lens system further comprises:
a first substrate; and
a second substrate, the second substrate being sandwiched between the second lens and the third lens.

16. The capsule endoscope of claim 15, wherein:
the first lens further comprises a planar surface in contact with the first substrate;
the second lens further comprises a planar surface in contact with the second substrate; and
the third lens further comprises a planar surface in contact with the second substrate.

17. The capsule endoscope of claim 16, further comprising a stop interposed between the second substrate and the third lens.

18. The capsule endoscope of claim 16, wherein a field of view of the lens system is greater than 110°.

19. The capsule endoscope of claim 16, wherein a total length of the lens system from an outer surface of the first substrate to an image plane is less than 2.1 mm.

20. The capsule endoscope of claim 16, wherein a focal length of the lens system is equal to or less than 0.43 mm.

21. The capsule endoscope of claim 16, wherein an F-number of the lens system is equal to or less than 4.

22. The capsule endoscope of claim 16, wherein a diameter of light rays at an image plane of the lens system is less than 1.0 mm.

23. The capsule endoscope of claim 16, wherein each of the first substrate and the second substrate has two parallel planar surfaces.

* * * * *